United States Patent [19]

Tanaka et al.

[11] Patent Number: 4,525,069

[45] Date of Patent: Jun. 25, 1985

[54] OPTICAL ABSORPTION ANALYZER

[75] Inventors: Masaru Tanaka; Naoki Noguchi; Kenji Yoshino; Osamu Saitoh, all of Kyoto, Japan

[73] Assignee: Horiba, Ltd., Kyoto, Japan

[21] Appl. No.: 371,484

[22] Filed: Apr. 23, 1982

[30] Foreign Application Priority Data

May 19, 1981 [JP] Japan ................... 56-75120

[51] Int. Cl.³ ............................................ G01N 21/61
[52] U.S. Cl. ..................................... 356/435; 250/565; 356/437
[58] Field of Search ............... 356/319, 435, 448, 222, 356/229, 437; 250/458.1, 461.1, 461.2, 564, 565

[56] References Cited

U.S. PATENT DOCUMENTS 4,055,768 10/1977 Bromberg ................ 250/461.2
4,320,970 3/1982 Dowben et al. ........... 250/458.1 X Primary Examiner—F. L. Evans
Attorney, Agent, or Firm—Wenderoth, Lind & Ponack

[57] ABSTRACT

An optical absorption analyzer for determining the concentration of low concentration components of a sample gas. Inexpensive voltage to frequency converters, up/down counters, and integrators are used to obtain a high accuracy determination which is independent of fluctuations in the strength of the light source used in the analyzer.

6 Claims, 6 Drawing Figures

OPTICAL ABSORPTION ANALYZER

BACKGROUND OF THE INVENTION

1. Field of the Invention

The present invention relates to an optical absorption analyzer for determining the concentrations of components to be determined by means of an optical absorption method; in particular the present invention relates to an optical absorption analyzer which is capable of determining the components such as ozone and the like which have extremely low concentrations and which are contained within the atmosphere.

2. Description of the Prior Art

In the determination of the concentration of ozone contained within the atmosphere by means of an optical absorption method, ozone, having a concentration of 1 ppm, for example, only absorbs about 0.1% of the quantity of transmitted light. However, the strength of the light source used also fluctuates by 0.1% which is the same order of magnitude as the absorption of light by the ozone. Accordingly, it is impossible to determine the concentration of ozone by means of the usual optical absorption method.

Japanese unexamined patent application (laid-open No.: 29,176/1976) discloses a measuring circuit for determining the concentration of ozone so as to eliminate the effects of fluctuations in the strength of the light source. In principle, this circuit, as shown in FIG. 1, consists of a detector 2 for detecting light transmitted through a measuring cell 1, a detector 4 for directly detecting light emitted from a light source 3, voltage to frequency converters 5 and 6 for converting the voltage signals generated by the detectors 2 and 4, and up/down counters 7 and 8 for counting the pulse signals output from the converters 5 and 6. In operating this circuit, a zero gas is fed into the measuring cell 1 prior to the measurement determination. The signals, which are obtained from detectors 2 and 4 and then converted to pulse signals by the voltage/frequency converters 5 and 6, are then counted up by counters 7 and 8. Counters 7 and 8 are stopped when the count stored in the counter 7, (as shown by a polygonal line 7' in FIG. 2(a); the polygonal line 8' shown in FIG. 2(b) showing the count stored in the counter 8), reaches a definite value, for example, a value of K.

Then, the gas to be measured is introduced into the measuring cell 1; the pulse signals, which are output from the voltage/frequency converters 5 and 6, are input to counters 7 and 8 so as to count down from the previously stored count. Finally, counters 7 and 8 are stopped when the count stored in counter 8 becomes equal to zero. The count v stored in counter 7 (see FIG. 2(a), at the stoppage of counting is used as an output datum. The count v is calculated by the equation:

$$v = Kclx,$$

assuming that the length of the measuring cell 1 is l, the concentration of gas is x, and the absorption coefficient is c.

According to this prior art, the influence of the fluctuations in the strength of the light source can be eliminated because a method is adopted in which the quantity of light is integrated until the definite value is reached. Thus, it is possible to accurately determine components, such as ozone and the like, having extremely low concentrations.

However, this prior art has a defect in that two voltage/frequency converters must both have an accuracy of the same order of magnitude as the above-noted concentration and, furthermore, two up/down counters must be able to count up to such a magnitude. Accordingly, such an apparatus is extremely expensive if it is necessary to make the measurement determination of components having an extremeley low concentration. For example, the determination of ozone of a concentration 1 ppm at an accuracy of 0.1% requires the determination of the quantity of light emitted from a light source at the accuracy of $10^{-6}$ and it is thereby necessary to provide a voltage/frequency converter having an accuracy on the order of $10^{-6}$. Consequently, it is necessary to use an up/down counter which can store six-digit numbers. Although an analog integrator may be substituted for the voltage/frequency converter and the up/down counter included in the circuit shown in FIG. 1, an accuracy on the order of $10^{31\ 6}$ is required for the integrator, so as to thereby result in an expensive instrument.

SUMMARY OF THE INVENTION

The present invention can provide an optical absorption analyzer in which two voltage/frequency converters, up/down counters and integrators, may be inexpensive units which do not require a very high accuracy and large number of digits, but can accurately determine components, such as ozone and the like, having an extremely low concentration without being influenced by fluctuations in the strength of the light source.

The present invention relates to an optical absorption analyzer consisting of a light source, two optical detectors and at least one cell arranged in an optical path between the light source and the optical detectors, wherein a first process passes one of either a zero gas and a sample gas to be measured through the cell and a second process passes the gas not used in the first process through the cell. A gain control circuit is provided for controlling the amplitude of the signal output by the first optical detector. A differential amplifier is provided for amplifying the difference between the signal output from the first optical detector and the signal output by the second optical detector. An integrator is included for integrating the signal output by the second optical detector and for providing an agreement signal when the integrated value reaches a predetermined value. A signal processing circuit means, connected to the differential amplifier and having an integrating, storing and comparing function is also included. In the first process, the gain of the gain control circuit is adjusted and fixed so that the signal output by the first optical detector may be equal to the signal output by the second optical detector with a predetermined accuracy, the signal with the fixed gain arises from the differential amplifier and is integrated from the time when the integrator begins to integrate to the time when the integrator provides the agreement signal by means of the signal processing circuit means, and the resulting integrated value is subsequently stored. In the second process, the signal arises from the differential amplifier with the gain adjusted and fixed by means of the gain control circuit in the first process and is integrated by means of the signal processing circuit means from the time when the integrator begins to integrate to the time when the integrator provides the agreement signal, and the resulting integrated value is subsequently compared with the integrated value stored in the first process so as to analyze the components to be analyzed. The method of arranging the cell in the optical path between the light source and the detector includes the single-cell method in which only one cell is arranged in the optical path between the light source and the detector, and the double-cell method in which separate cells are respectively arranged in the optical paths between the light source and the two detectors. In case of the single-cell method, the cell may be arranged in the optical path between the light source and the first detector or the optical path between the light source and the second optical detector. In addition, a zero gas is passed through the cell in the first process while the gas to be measured is passed through the cell in said second process, in the case of the single-cell method. On the other hand, the double-cell method includes an arrangement in which a zero gas is continuously passed through one cell while a zero gas is passed through another cell in the first process and the gas to be measured is passed through another cell in the second process, and includes the arrangement in which a zero gas is passed through one cell and the gas to be measured is passed through another cell in the first process while the gas to be measured is passed through one cell and zero gas is passed through another cell in the second process by changing over the flow of gas. Nitrogen gas or refined air is used as the zero gas. But, it is desirable to use the gas, from which only the components to be determined were removed (the interference components remaining) by passing the gas to be measured through a zero gas refiner, as the zero gas to be used in the double-cell method. Either method of arranging the cell can be used for carrying out the present invention.

DESCRIPTION OF THE PREFERRED EMBODIMENTS

Figure 3:
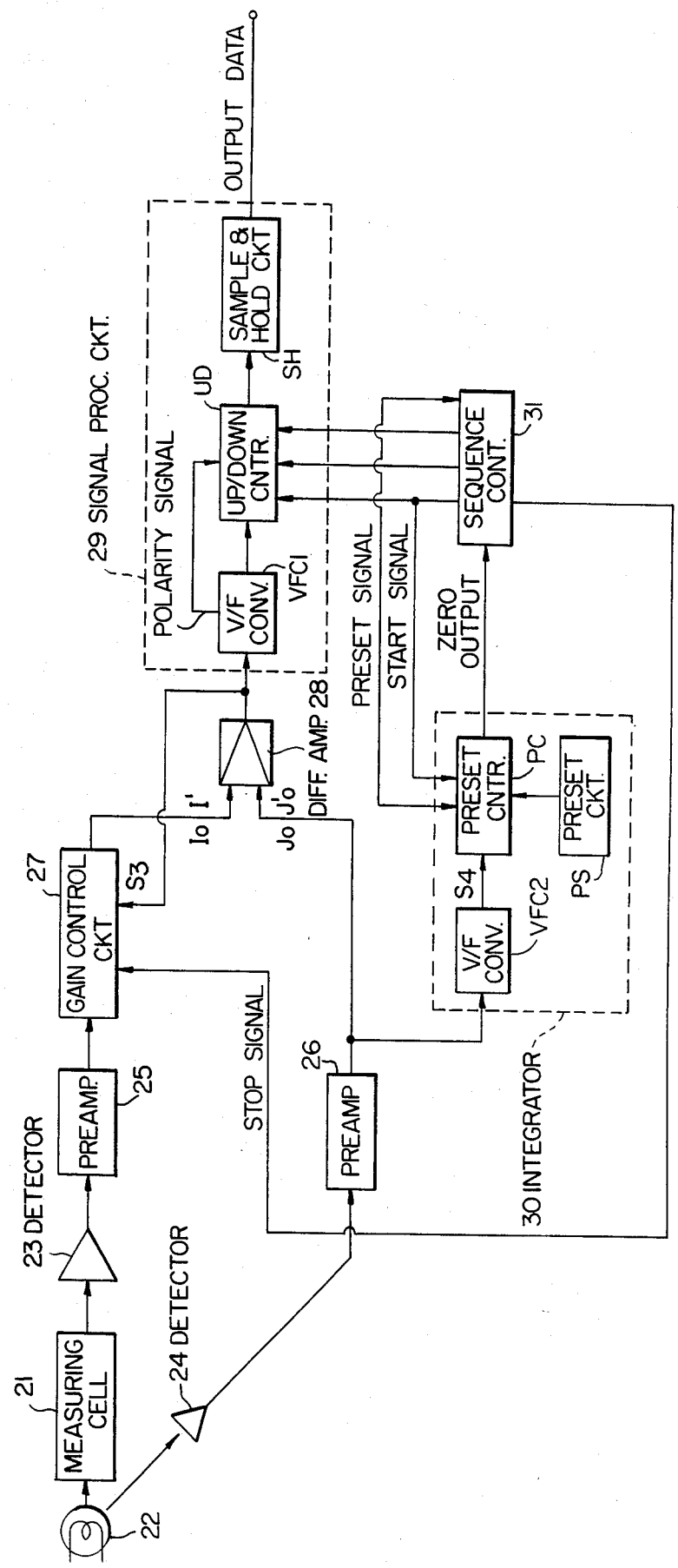
FIG. 3 is a block diagram showing an example of the present invention.

FIG. 3 shows an example in which the present invention was applied to the single-cell method, wherein a cell 21 is arranged in an optical path between a light source 22 and a first optical detector 23. Referring to FIG. 3, element 24 is a second optical detector, elements 25 and 26 are preamplifiers, element 27 is a gain control circuit, element 28 is a differential amplifier, and element 29 is a signal processing circuit means. In the preferred embodiment, as shown in FIG. 3, the circuit means 29 consists of a voltage/frequency converter $VFC_1$, an up/down counter UD and a sample and hold circuit SH. Element 30 is an integrator which consists of a voltage/frequency converter $VFC_2$, a preset counter PC and a preset circuit PS in the preferred embodiment, as shown in FIG. 3. Element 31 is a sequence controller for operating the circuits on the basis of the signals arising from the circuits. The above-noted constituent elements carry out the required operations by means of the actions of the controller in the first process and the second process as described below.

The first process is carried out as follows:

At first, a zero gas is passed through the cell 21. At this time, the difference between the signal $I_o$ obtained from the first detector 23 and output from the gain control circuit 27 and the preamplifier 26 is amplified by means of the differential amplifier 28 and the gain of the gain control circuit 27 is adjusted by an output signal from the differential amplifier 28 so that the value of the signal $I_o$ may be equal to that of the signal $J_o$ at a predetermined accuracy. The adjusted gain is fixed by a stop signal output from the sequence controller 31 after the adjustment. It is desirable to select a predetermined accuracy of $10^{-3}$ when a measuring accuracy of $10^{-6}$ is desired. The signal $I_o$ is equal to the signal $J_o$ at an accuracy of up to $10^{-3}$ if the gain of the gain control circuit 27 is adjusted at such an accuracy. It can, however, not be said that the signal $I_o$ is equal to the signal $J_o$ at an accuracy of an order higher than such an order, that is, at the accuracy of $10^{-4}$ to $10^{-6}$. Accordingly, an output of the differential amplifier 28 includes an unequal signal of up to $10^{-4}$ to $10^{-6}$ which is the difference between the signal $I_o$ and the signal $J_o$. However, the signal value of the difference between the signal $I_o$ and the signal $J_o$ is not so weak as $10^{-4}$ to $10^{-6}$ times $I_o$, $J_o$ but is amplified to the same degree as the first signal $I_o$, $J_o$ because the coefficient of amplification of the differential amplifier 28 is 1,000 or more.

Figure 4:
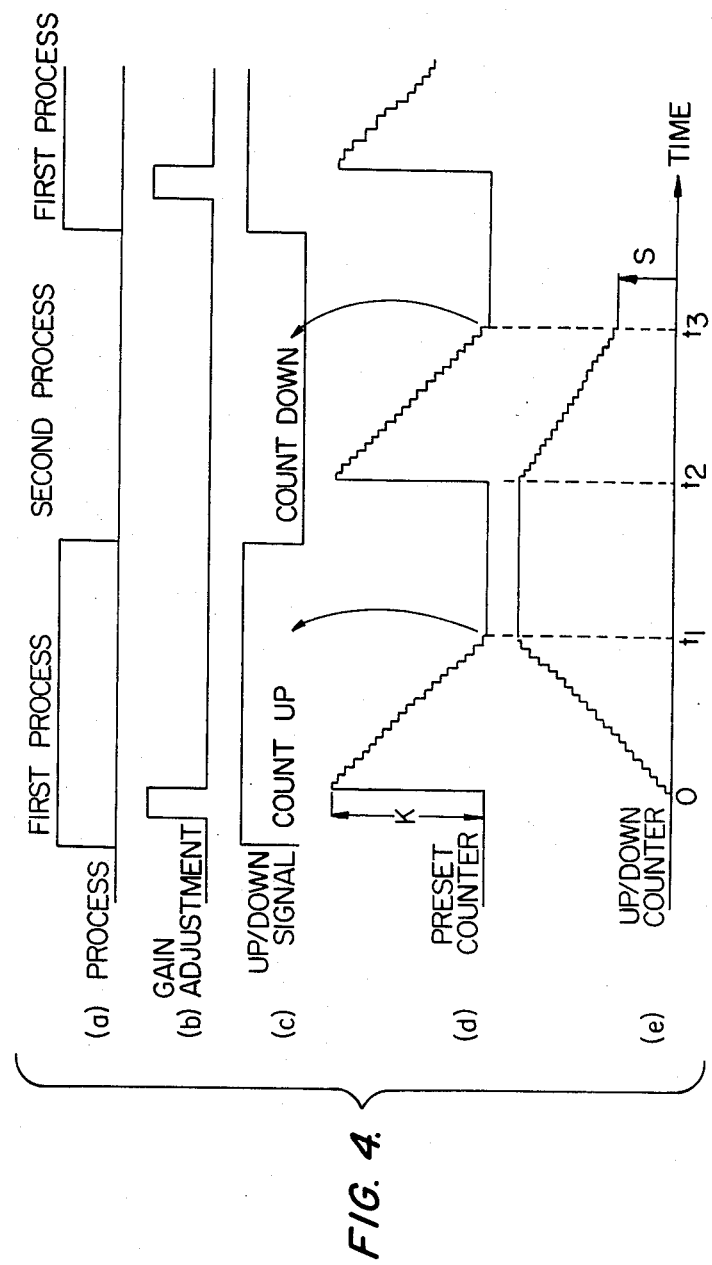
FIG. 4 is a diagram for explaining the measuring operation of the analyzer shown in FIG. 3.

Then, the sequence controller 31 provides the start signal to the preset counter PC and the up/down counter UD after the gain of the gain control circuit 27 was adjusted and fixed. The preset counter PC is initially set to a predetermined value (the value corresponding to the definite value in the above-described prior art; hereinafter referred to as K), which was set for the preset circuit PS on the basis of a preset signal and accordingly, the start signal subtracts a pulse signal, which is obtained from the second detector 24 through the voltage/frequency converter $VFC_2$, from the predetermined value K (refer to FIG. 4(d)). On the other hand, the up/down counter UD begins to count up a pulse signal, which is obtained from the differential amplifier 28 from the voltage/frequency converter $VFC_1$, as soon as the start signal is provided (refer to FIG. 4(e)). When the contents of the preset counter PC becomes equal to zero, a zero output is fed to the sequence controller 31 and a count stop instruction is fed to the up/down counter UD from the controller 31 to stop counting. The first process is over at this point. After the first process is over, the preset counter PC is again initially set to the predetermined value K prior to the performance of the second process. In addition, the counter UD is changed over so as to count down.

In the second process, the measuring gas instead of the zero gas is passed through the cell 21. The light, which passed through the measuring gas, is detected by means of the first detector 23 and the detected signal is fed to the differential amplifier 28 and output from the gain control circuit 27 for the gain adjusted and fixed in the first process. A signal $J_o'$ obtained by directly detecting a light output from the light source 22 is fed to the differential amplifier 28 and the signal corresponding to the difference between the signal $J_o'$ and the signal I, which passed through the gain control circuit 27, is thereby amplified and output from the differential amplifier 28. The resulting output signal ($I' - J_o'$) is fed to the counter UD through the voltage/frequency converter $VFC_1$ as a count down signal. However, the time when counting down begins and the time when counting down is completed is coincident with the time when the preset counter PC begins to count down and the time when zero output is output, as is respectively similar to the first process. The count value S remaining in the counter UD at the time when the preset counter PC provides a zero output is the value showing the concentration of the components to be determined which is held in the sample and hold circuit SH and output as output date.

As is represented by the following equations, the count value S remaining in the counter UD shows the concentration of the components to be determined:

On the assumption that the signal $I_{o(t)}$ (t being time, and therefore, $I_{o(t)}$, $J_{o(t)}$, $J_o'(t)$ and $I'(t)$ being functions of time) designates the signal obtained from the gain control circuit 27 (hereinafter referred to as the first detector side) and $J_{o(t)}$ designates the signal obtained from the preamplifier 26 (hereinafter referred to as the second detector side) in the first process; $I'(t) = I_o'(t)e^{-alx}$ designates the signal obtained from the first detector side and $J_o'(t)$ designates the signal obtained from the second detector side in the second process; and $I_{o(t)}/J_{o(t)} = I_o'(t)/J_o'(t) = d$.

The preset counter PC acts during the time ($t_1$) defined by the following equation (1) in the first process.

$$\int_o^{t_1} J_{o(t)} dt = K \tag{1}$$

The counter UD also acts during the time ($t_1$) and the stored count is thereby represented by the following equation (2).

$$\int_o^{t_1} \{I_{o(t)} - J_{o(t)}\} dt = B \tag{2}$$

Then, the preset counter PC acts during the time ($t_3 - t_2$) defined by the following equation (3).

$$\int_{t_2}^{t_3} J_o'(t) dt = K \tag{3}$$

The following equation (4) is obtained by subtracting equation (3) from equation (1):

$$\int_o^{t_1} J_{o(t)} dt - \int_{t_2}^{t_3} J_o'(t) dt = 0 \tag{4}$$

On the other hand, counter UD is counted down from the preceding count value during the time ($t_3 - t_2$). Accordingly, the content S becomes equal to the value represented by the following equation (5).

$$\int_o^{t_1} \{I_{o(t)} - J_{o(t)}\} dt - \int_{t_2}^{t_3} \{I'(t) - J_o'(t)\} dt = S \tag{5}$$

Equation (5) may be rewritten as the following equation (6).

$$\begin{aligned} S &= (\alpha - 1) \int_o^{t_1} J_{o(t)} dt - (\alpha e^{-alx} - 1) \int_{t_2}^{t_3} J_o'(t) dt \\ &= (\alpha - 1) \int_o^{t_1} J_{o(t)} dt - (\alpha e^{-alx} - 1) \int_o^{t_1} J_{o(t)} dt \\ &= K(\alpha - 1) - K(\alpha e^{-alx} - 1) \\ &= K\alpha(1 - e^{-alx}) \end{aligned} \tag{6}$$

In the case of components of low concentration, equation (6) may be written as the following equation (7).

$$S = K\alpha \cdot alx \tag{7}$$

From a long-term viewpoint, $\alpha$ is changed because it is a function of time. However, it is apparent from the above-noted description that the value of $\alpha$ can be kept constant by adjusting the gain every cycle by means of the gain control circuit 27 from the start of the first process until the completion of the second process (the time when the preset counter PC provides a zero output). Consequently, it is possible to determine the concentration x of the components to be determined from the value of S on the basis of equation (6) or equation (7).

However, according to the above-described construction, the gain of the gain control circuit 27 is adjusted so that the first detector side signal may be equal to the second detector side signal at a predetermined accuracy ($10^{-3}$) and fixed during one cycle and it is thereby only necessary that the voltage/frequency converter $VFC_1$ and the counter UD forming the signal processing circuit means 29 can convert and count the signals, which could not be equalized by means of the gain control circuit means 27 or have an order ($10^{-4}$ to $10^{-6}$) not guaranteed against the agreement thereof. Accordingly, the accuracy, which is obtained by dividing the accuracy ($10^{-6}$) required for the determination by the accuracy ($10^{-3}$) of the gain control circuit 27, is sufficient for the accuracy of the voltage/frequency converter $VFC_1$ and the number of digits (3 digits), which is equal to the value of an exponent of the accuracy required for the voltage/frequency converter $VFC_1$, is sufficient for the number of digits of the counter UD. In addition to the above-described reason, another reason why such a lower accuracy and small number of digits are sufficient for the voltage/frequency converter $VFC_1$ and the counter UD is that the concentration of the components to be determined is low, i.e.—on the order of 1 ppm. That is to say, it is because the process is based on the premise that the concentration of the components to be determined is low and the signal corresponding to the difference between $I_{o(t)}$ and $J_{o(t)}$ in the first process is thereby adjusted so as to be equal to the signal of the difference between $I_o'(t)$ and $J_o'(t)$ in the second process at the same accuracy range as the gain control circuit 27. It is natural that it is only necessary to suitably define the accuracy of the gain control circuit 27 in accordance with the point at which the two signals approximately coincide with each other.

According to this preferred embodiment, the signal processing circuit means 29 consists of digital circuits such as the voltage/frequency converter $VFC_1$, the up/down counter UD, and the like. But analog circuits also may be used. In this case, a signal processing circuit means may consist of an integrator for integrating the analog signals arising from the differential amplifier 28, a register for storing the integrated value obtained in the first process and a differential amplifier for obtaining the difference between the integrated value in the second process and the stored value of the register. Also, an analog integrator can be substituted for a digital integrator.

Figure 1:
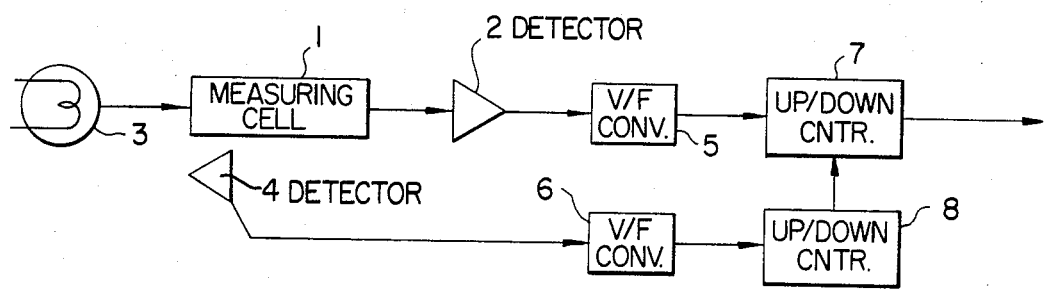
FIG. 1 is a block diagram of a conventional optical absorption analyzer.
Figure 2:
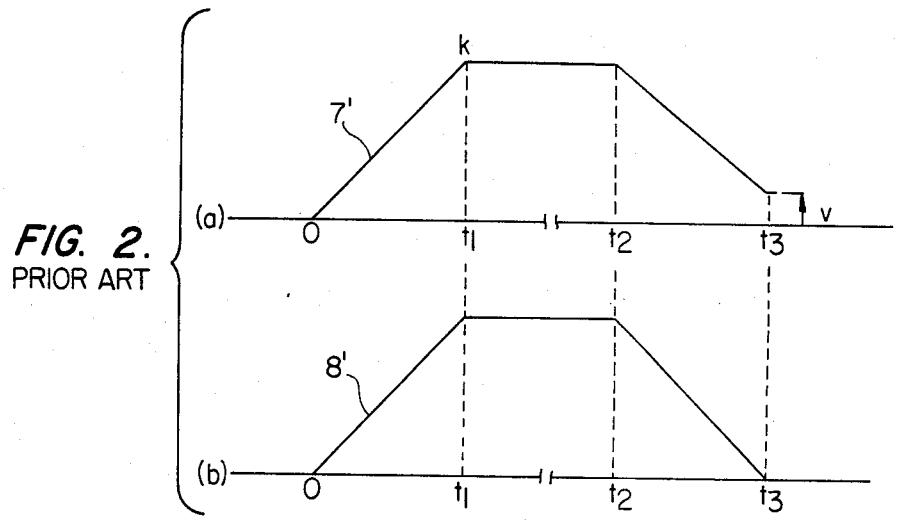
FIGS. 2(a)-2(b) are waveform diagrams for explaining the measuring operation of the analyzer shown in FIG. 1.
Figure 5:
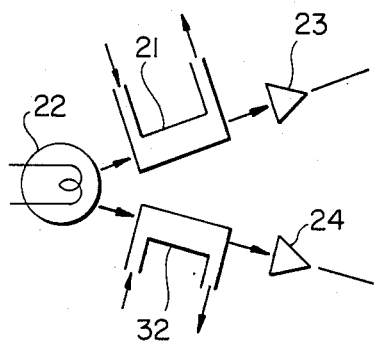
FIG. 5 is a diagram showing the cell type for which the present invention is applicable.

Described below is another preferred embodiment of the present invention, in which the double-cell method is disclosed as being provided with two separate cells 21 and 32 arranged in two optical paths between the light source 22 and having two detectors 23 and 24 as shown in FIG. 5. As described above, the double-cell method includes the method, in which a zero gas is passed through one cell while a zero gas is passed through a second cell in the first process and the measuring gas is passed through the second cell in the second process (hereinafter simply referred to as the double-cell method), and the method, in which a zero gas and the measuring gas are passed through both cells alternatively (hereinafter referred to as the cross-flow method). Hereinafter, these methods will be described in turn.

THE DOUBLE CELL METHOD

A zero gas is passed through cell 32 while a zero gas and the measuring gas are passed through cell 21 alternatively during every process. However, the zero gas is obtained by passing the measuring gas through the zero gas refiner and it thereby contains the interference components. Assuming that the coefficient of absorption of the interference components is b and the concentration thereof is y, the signal from the first detector side is $I_{o(t)}e^{-bly}$ in the first process and $I_{o'(t)}e^{-alx-bly'}$ in the second process because Lambert-Beer's law is applicable also to the interference components in general. Similarly, the signal from the second detector side is $J_{o(t)}e^{-bly}$ in the first process and $J_{o'(t)}e^{-bly'}$ in the second process. These equations can be written in the form of the following equation (8) by treating them similarly to the above-described equations (1) to (6), wherein $$\alpha = I_{o(t)}/J_{o(t)} = I_{o'(t)}/J_{o'(t)}. \tag{8}$$

$$K = \int_0^{t_1} J_{o(t)}e^{-bly}dt = \int_{t_2}^{t_3} J_{o'(t)}e^{-bly'}dt$$

$$S = \int_0^{t_1} \{I_{o(t)}e^{-bly} - J_{o(t)}e^{-bly}\}dt$$

$$- \int_{t_2}^{t_3} \{I_{o'(t)}e^{-alx-bly'} - J_{o'(t)}e^{-bly'}\}dt$$

$$= (\alpha - 1) \int_0^{t_1} J_{o(t)}e^{-bly'}dt$$

$$- \{\alpha e^{-alx} - 1\} \int_{t_2}^{t_3} J_{o'(t)}e^{-bly'}dt$$

$$= K(\alpha - 1) - K\{\alpha e^{-alx} - 1\}$$
$$= K\alpha(1 - e^{-alx})$$

Equation (8) has the same form as equation (6). This shows that the double-cell method can also determine the concentration of the components to be determined. In addition, the double-cell method has an advantage in that the influences of the interference components are compensated for and the output is thereby not influenced by such interference components.

Although the zero gas and the measuring gas are passed through one cell 21 alternatively in this example, the other method, in which the zero gas is passed through one cell 21 while the zero gas and the measuring gas are passed through another cell 32 alternatively, also can similarly compensate for the influences of the interference components so as to determine the concentration of the components to be determined.

THE CROSS-FLOW METHOD

Referring now to FIG. 5, the measuring gas is passed through one cell 21 while the zero gas is passed through another cell 32 in the first process and the zero gas is passed through one cell 21 while the measuring gas is passed through another cell 32 in the second process. In this case, the following equation (9) is formed:

$$\int_0^{t_1} J_{o(t)}e^{-alx} \cdot e^{-bly}dt = K \tag{9}$$

$$= \int_{t_2}^{t_3} J_{o'(t)}e^{-bly'} dt$$

$$S = \int_0^{t_1} \{GI_{o}e^{-bly} - J_{o}e^{-alx} \cdot e^{-bly'}\}dt$$

$$- \int_{t_2}^{t_3} \{GI_{o'(t)}e^{-alx} \cdot e^{-bly'} - J_{o'(t)}e^{-bly'}\}dt$$

$$= G\alpha \int_0^{t_1} J_{o(t)}e^{-bly}dt - K$$

$$- G\alpha e^{-alx} \int_{t_2}^{t_3} J_{o'(t)}e^{-bly'} + K$$

$$= G\alpha \cdot \frac{K}{e^{-alx}} - G\alpha e^{-alx} \cdot K$$

$$= G\alpha K \left( \frac{1}{e^{-alx}} - e^{-alx} \right)$$

(wherein G designates a gain adjusted by means of the gain control circuit 27)

Since the gain is adjusted by means of the gain control circuit 27, then:

$$GI_{o(t)}e^{-bly} = J_{o(t)}e^{-alx} \cdot e^{-bly}$$

and therefore $G\alpha = e^{-alx}$

Accordingly, equation (9) may be represented by the following equation (10):

$$S = K(1 - e^{-2alx}) \tag{10}$$

This equation (10) has the same form as equation (8) excepting that the exponent of e is doubled. Accordingly, this method can also compensate the influences of the interference components and determine the concentration x of components to be determined. In addition, this cross-flow method guarantees a more accurate determination because the exponent is doubled as described above and the output is thereby doubled.

Furthermore, although the detailed description has been omitted, the same result as equation (6) can also be approximately obtained in the single-cell method in which cell 21 is arranged in the optical path between the light source 22 and the second detector 24 in a fashion opposite to the construction shown in FIG. 3.

The present invention can exhibit such an effect that the components of low concentration can be determined at a high accuracy using the usually available low accuracy instruments for a signal processing circuit means and an apparatus can be constructed inexpensively because the signal from the first optical detector side and the signal from the second optical detector side are adjusted and fixed by means of the gain control circuit so that the signal from the first optical detector side may be equal to the signal from the second optical detector up to the predetermined accuracy.

What is claimed is:

1. An optical absorption analyzer for determining the concentration of a particular component of a gas mixture, said analyzer comprising:

a light source;

first and second optical detectors and at least one cell arranged in an optical path between said light source and said first and second optical detectors, said detectors and at least one cell arranged such that during a first process, one of either a zero gas and a sample gas to be measured is passed through said at least one cell and, during a second process, the gas different from that of said first process is passed through said at least one cell;

a gain control circuit connected to an output of said first optical detector for controlling the amplitude of a first signal which is output by said first optical detector;

a differential amplifier connected to outputs of said gain control circuit and said second optical detector for amplifying the difference between said first signal and a second signal which is output by said second optical detector, said differential amplifier having an output which is fed back to said gain control circuit for controlling the operation thereof;

an integrator connected to said output of said second optical detector for integrating said second signal and for outputting an agreement signal when the integrated value reaches a predetermined value; and a signal processing circuit means having an input connected to an output of said differential amplifier and having means for integrating, storing and comparing signals input thereto;

wherein, during said first process, the gain of said gain control circuit is controlled so that said first signal from said first optical detector is equal in value to said second signal from said second optical detector at a predetermined accuracy, and said output from said differential amplifier is integrated by said signal processing means from an instant of time when said integrator begins to integrate to an instant of time when said integrator outputs said agreement signal which is input to said signal processing means and the resulting integrated value is stored by said signal processing circuit means; and wherein, during said second process, said signal output from said differential amplifier is integrated by said signal processing circuit means from an instant of time when said integrator begins to integrate to an instant of time when said integrator outputs said agreement signal, and the resulting integrator value is then compared with said integrated value stored during said first process so as to analyze said component to be analyzed.

2. An optical absorption analyzer as set forth in claim 1, wherein said at least one cell comprises first and second cells which are separately arranged in two optical paths between said light source and said first and second optical detectors, and wherein said zero gas is continuously passed through said first cell while said zero gas is passed through a second cell during first process and said sample gas is passed through said second cell during said second process.

3. An optical absorption analyzer as set forth in claim 1, wherein said at least one cell comprises first and second cells which are separately arranged in two optical paths between said light source and said first and second optical detectors, and wherein said zero gas is passed through said first cell while said sample gas is passed through said second cell in said first process and said sample gas is passed through said first cell while said zero gas is passed through said second cell in said second process.

4. An optical aborption analyzer as set forth in any one of claims 1 to 3, further comprising a sequence controller means having inputs connected to said integrator and having outputs connected to control inputs of said gain control circuit and said integrator and said processing circuit means for controlling the operation of said analyzer during said first process and said second process.

5. An optical absorption analyzer as set forth in any one of claims 1 to 3, wherein said integrator and said signal processing circuit means comprise digital circuit elements for digitally performing said integrating and processing.

6. An optical absorption analyzer as set forth in claim 4, wherein said integrator and said signal processing circuit means comprise digital circuit elements for digitally performing said integrating and processing.

* * * * *